United States Patent [19]

Schmitt

[11] Patent Number: 5,259,392
[45] Date of Patent: Nov. 9, 1993

[54] BLOOD COLLECTION DEVICE

[75] Inventor: Robert J. Schmitt, Kenosha, Wis.

[73] Assignee: Abbott Laboratories

[21] Appl. No.: 729,133

[22] Filed: Jul. 12, 1991

Related U.S. Application Data

[63] Continuation of Ser. No. 526,859, May 21, 1990.

[51] Int. Cl.$^5$ .................................................. A61B 5/00
[52] U.S. Cl. ..................................... 128/763; 604/194; 604/195
[58] Field of Search ............... 604/192, 194, 198, 195, 604/200, 201, 110, 403, 263, 197; 128/763-766

[56] References Cited

U.S. PATENT DOCUMENTS

| | | | |
|---|---|---|---|
| 4,519,402 | 5/1985 | Andersen | 128/765 |
| 4,731,059 | 3/1988 | Wanderer et al. | 604/192 |
| 4,840,619 | 6/1989 | Hughes | 604/187 |
| 4,892,107 | 1/1990 | Haber | 128/763 |
| 4,911,693 | 3/1990 | Paris | 604/192 |
| 4,927,018 | 5/1990 | Yang et al. | 604/110 |
| 4,984,580 | 1/1991 | Wanamaker | 128/763 |
| 5,019,051 | 5/1991 | Hake | 604/198 |
| 5,074,888 | 12/1991 | Burt et al. | 604/265 |

*Primary Examiner*—Robert A. Hafer
*Assistant Examiner*—Sam Rimell
*Attorney, Agent, or Firm*—Daniel R. Curry

[57] ABSTRACT

The present invention involves an integrated double-ended needle and blood collection device assembly which is convenient to use, safely contained and ready for disposal after use. The device allows the user to expose and resheath potentially infectious needles without bringing the user's fingers or hands into close proximity with sharp or broken needle tips. After removing the needle from the patient, the needle is safely resheathed by retracting the needle into the device, thereby reducing the risks of accidental needle wounds and infection. The device also serves as a holder for blood collection tubes which can be easily inserted and removed for multiple sampling.

11 Claims, 2 Drawing Sheets

BLOOD COLLECTION DEVICE

This is a continuation application of U.S. Ser. No. 07/526,859, filed on May 21, 1990.

BACKGROUND OF THE INVENTION

1. Field of the Invention

The present invention relates to an integrated assembly and apparatus for the collection of multiple samples of blood specimens. The invention further relates to an apparatus for drawing blood samples, wherein a double-ended needle is sheathed before use and safely resheathed after use, thereby reducing the risk of accidental needle wounds and resultant infections to a minimum. In another aspect, the invention relates to a blood collection device and integrated double-ended needle, wherein at no time is it necessary to cap or cut-off an exposed needle after use.

2. Related Art

Apparatus typically used to perform phlebotomy are septum-capped evacuated tubes which are used with double-ended hollow needles or sharpened cannulae, one end of which is inserted into the patient and the other end pierces the septum, thereby withdrawing a volume of blood. Prior to disposal of the needle, the needle is either capped or broken-off to prevent reuse.

It is customary to use sterile, single use, disposable devices for taking blood samples from patients just as single use, disposable, sterile hypodermic needles are widely used for administering therapeutic agents. While these conventional single use, disposable devices fully protect the patient from the dangers of infectious diseases, such as AIDS and certain hepatitis viruses, they present a risk of infection to medical and hospital personnel due to accidental wounding with a contaminated needle or contact with other contaminated parts of the disposable apparatus. Normally, health care workers are especially susceptible to accidental and potentially infectious needle wounds due to the careless handling or breaking of the needle in disposing of the syringe after use. Accidental needle wounds generally result in the need for blood tests for such diseases as AIDS and hepatitis. The corresponding costs and inefficiency of testing health care workers who have received an inadvertent needle wound result in a considerable waste of resources, which may be particularly damaging to a health care facility, as well as an ever present danger to the worker personally.

Widely used commercial devices for blood collection include double-ended, multiple sample needles having protective caps over both needle ends for storage. The needle holder for such a needle is often separate from the needle and reusable. The risk of a needle wound to the user, especially when recapping the needle after drawing a sample, is unacceptably high. In addition, the destruction of the needle in a clipping device has been recommended, but this is also a hazardous practice because of aerosol production of contaminated blood samples, the continued risk of wounds from the resultant blunt needle shaft and the hazards uncapped needles present to waste disposal personnel. Furthermore, it is not always practical to carry a needle clipping device from patient to patient in a hospital or clinic environment.

SUMMARY OF THE INVENTION

The present invention involves a novel blood collection device suitable for use with a double-ended needle. The device includes a tube having forward and rear ends with at least one longitudinal external slot in the tube wall. The external slot terminates in a first transverse slot extension in the forward end portion of the tube and a second transverse slot extension in the rear end portion of the tube. The tube forward end terminates in a needle sheath which is axially aligned with the axis of the double-ended needle, and the tube rear end terminates with an open tube bore. The double-ended needle is mounted centrally and perpendicularly through a support member which is slideably positioned in the bore of the tube and is capable of movement along the tube bore between the tube forward end portion and the tube rear end portion. The support member has arm means secured thereto, wherein the arm means projects through the longitudinal external slot of the tube and is movable in a slideable and rotatable manner from one transverse slot extension to another transverse slot extension, thereby enabling the user to secure the support member in either a forward end position or a rear end position. When the support member is secured in the forward end position, the needle is extended from the device. When the support member is secured in the rear end position, the needle is withdrawn into the device.

The support member can be a substantially rigid disc which is rotatably and slideably encased within the tube bore. The disc has a center axis, axially aligned with the axis of the tube bore, and generally includes two finger tabs connected to the disc by the arm means which are slideably positioned in and through two longitudinal external slots in the tube wall. In a preferred embodiment of the invention, the transverse slot extensions include a detaining means whereby the movable arm is secured within the forward or rear transverse slot extension, thereby locking the needle in either an extended or sheathed position. After withdrawal of the needle from the patient, the finger tabs can be rotated, unlocked, pulled back and rotated into a retracted locked position either with or without the needle having been clipped. The entire assembly is then safely contained and ready for disposal.

In an alternative embodiment, the needle sheath can be capped or covered by needle sheath cap. For example, a holding ring on the needle sheath can be used to secure the sheath cap by interlocking with an interior groove on the sheath cap. In yet another embodiment, the device can include a handling flange at the rear end of the tube to facilitate manipulation of the device. In a further embodiment, the device includes a tube rear end cap to close the rear end of the tube, and optionally, the tube rear end cap can be connected to a needle sheath cap by a flexible connector.

In another preferred embodiment, the device can include an interior or exterior tube sleeve having at least one sleeve longitudinal slot which is opposed to and of equal length to the tube longitudinal external slot. The sleeve is rotatably mounted so that upon rotation the sleeve closes or covers the tube longitudinal external slot.

The integrated double-ended needle and blood collection device of the present invention provides an assembly which is highly simplified and convenient to use. The assembly also serves as a holder of blood collection tubes during sample taking, with the collection tubes being easily inserted and removed through the rear bore opening of the device.

BRIEF DESCRIPTION OF THE DRAWINGS

FIG. 4 further presents an optional outer sleeve which is rotatably mounted on the tube and covers the longitudinal external slots when the finger tabs are in either the retracted or the extended locked position.

DETAILED DESCRIPTION OF THE INVENTION

The present invention provides a novel blood sample device wherein the double-ended needle is completely sheathed in the device until needed for use. The hands or fingers of the user need never approach the needle either to place it into position for use or for resheathing and disposal. The object of the blood collection device is the protection of medical, hospital and clinical users or others who might come in contact with the device and integrated needle after use but prior to disposal.

Another object of the invention is to provide a blood collection device, having such safety features, and which is highly simplified and therefore, relatively economical to manufacture, convenient to use, reliable in its operation and construction and operable in such a way that the risk of spreading infection with a used device is significantly reduced. Other objects and advantages of the invention will become apparent to those skilled-in-the-art from the following detailed description.

Figure 1:
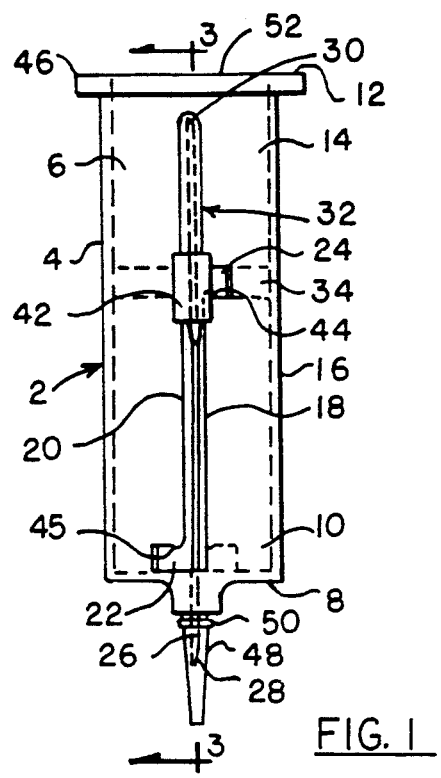
FIG. 1 is a side elevation view of the blood collection device of the present invention in a retracted and unlocked position.
Figure 2:
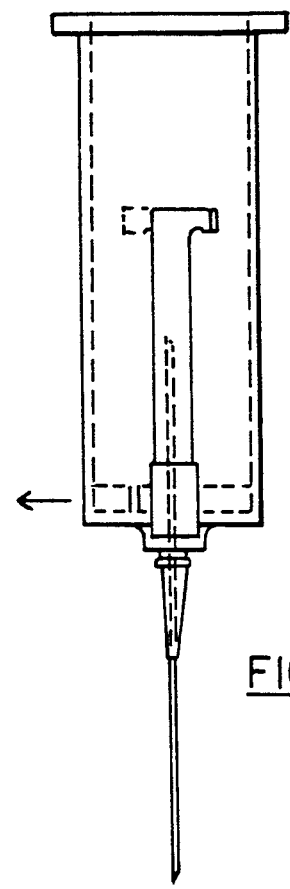
FIG. 2 is a side elevation view of the blood collection device with the needle in an exposed position for use. Locking is accomplished by rotating the finger tabs in the direction of the arrow.
Figure 4:
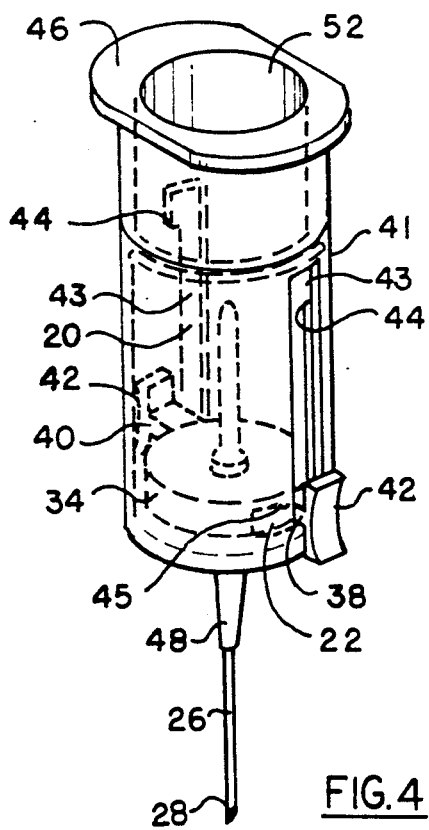
FIG. 4 is a perspective view of the apparatus with the sample needle fully extended from the sheath, but without the finger tabs in a locked position.

Referring to the drawings in detail, wherein like numbers designate like parts, two main embodiments of the blood collection device are illustrated: an embodiment without a sleeve, FIGS. 1 and 2; and an embodiment involving an exterior sleeve, FIG. 4. Although the depicted blood collection devices are particularly useful in vacuum tube phlebotomy, i.e., the drawing one or more samples of blood into individual evacuated blood collection tubes, it will be appreciated that the safety features of the present invention are also applicable to a syringe with which a fluid is administered to a recipient by means of appropriate injection procedures.

Referring initially to FIG. 1, a side elevation view of the device is depicted, with the double-ended needle retracted in a safety position for handling, shipping and disposal. The numeral 2 designates the integrated double-ended needle and blood collection device. The tube 4 is an elongated rigid cylindrical body having a central longitudinal tube bore 6. The tube 4 has a closed forward end 8 and a tube forward end portion 10. The tube 4 also has a tube rear end 12 and a tube rear end portion 14, with tube side wall 16 connecting tube rear end 12 and tube forward end 8. Within the tube side wall 16 are one or more longitudinal slots, such as longitudinal external slot 18 and longitudinal external slot 20 which are positioned in opposite geometry. Longitudinal slots 18 and 20 both include transverse slot extensions 22, in the forward end portion 10, which extensions are positioned circumferentially in the same direction from the longitudinal slots. The longitudinal slots 18 and 20 also have rear end portion transverse slot extensions 24 circumferentially extending from the longitudinal slots in the same direction as regard the rear end portion 14, but which extend in the opposite direction to transverse slot extensions 22 in the forward end portion 10.

The double-ended tubular needle 26 has a forward end 28 and a rear end 30. A resealable septum or cover 32 encloses the tubular needle rear end 30. The double-ended tubular needle 26 is mounted centrally and perpendicularly through rigid disc 34 or a similar support member means having a central axis 3.

The rigid disc 34, as further illustrated in FIG. 4, has arms 38 and 40 extending through longitudinal external slots 18 and 20 and connected to finger tabs 42. The finger tabs 42 and connecting arms 38 and 40 enable the positioning of the rigid disc 34 and mounted double-ended tubular needle 26 into a retracted and locked position through locking means 44, whereby the double-ended tubular needle is totally encased within the device. The finger tabs 42, through arms 38 and 40, are used to move the rigid disc 34 and double-ended tubular needle 26 forward from the retracted position. The arms are moved through longitudinal external slots 18 and 20 and into the transverse forward slot extensions 22. The arm means 38 and 40 lock in place through a detaining means 45 wherein the tubular needle forward end 28 is fully extended outside the tube 4.

The finger tabs, arm means and detention means for positioning and securing the needle support member in a rear or forward position can be comprised of several configurations. The slot extensions 22 and 24 can be constructed with detaining means 45 and 44, respectively, within the transverse extension slot to hold the finger tabs and connected arms in place, yet the arms can be easily unlocked through an upward or downward pressure on the finger tabs. Such a locking means is only one example of a simple yet effective method for securing the needle in its rear or forward position. The detaining means depicted in FIGS. 1 and 4 involves a projecting portion 45 and 44 in both the forward and rear slot extensions 22 and 24, respectively, but could alternatively be an indent or notch which secures the arms within the transverse slot extensions.

Figure 5:
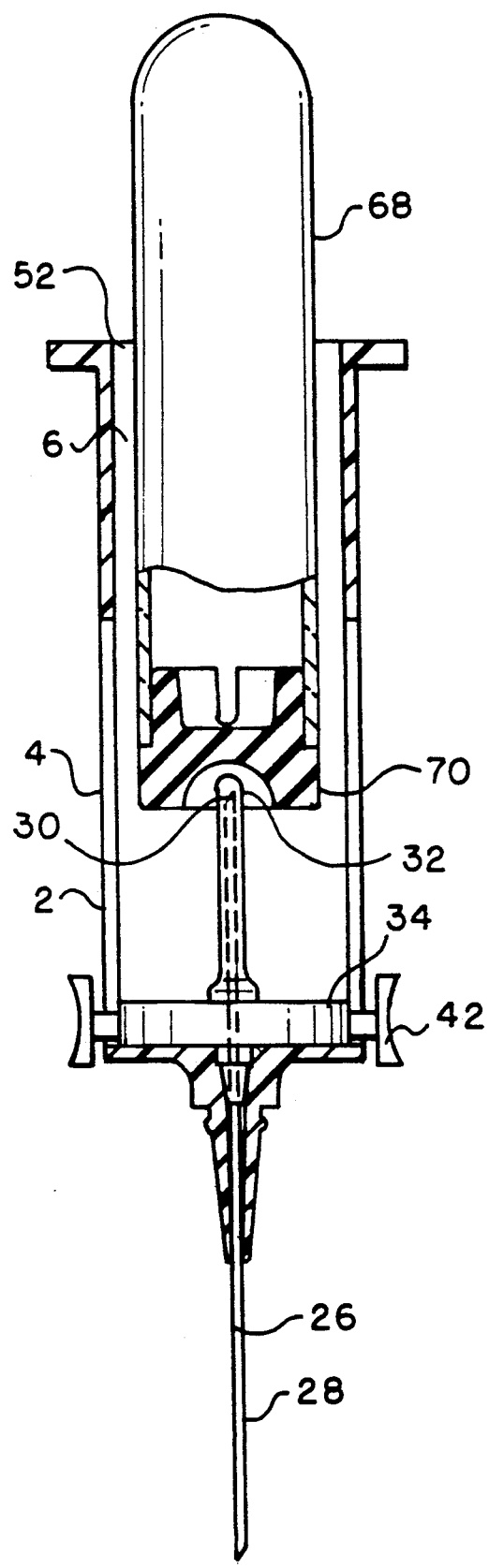
FIG. 5 depicts the blood collection device with the sample end of the needle fully extended from the device and an evacuated blood collection tube positioned above and ready for placement upon the resealable cover of the rear needle end.

A handling flange 46 can be positioned at the tube rear end 12 and can be placed surrounding the open tube bore 52. The flange is convenient for handling the device in general and as an aid for inserting and removing an evacuated phlebotomy tube 68, as shown in FIG. 5.

Figure 3:
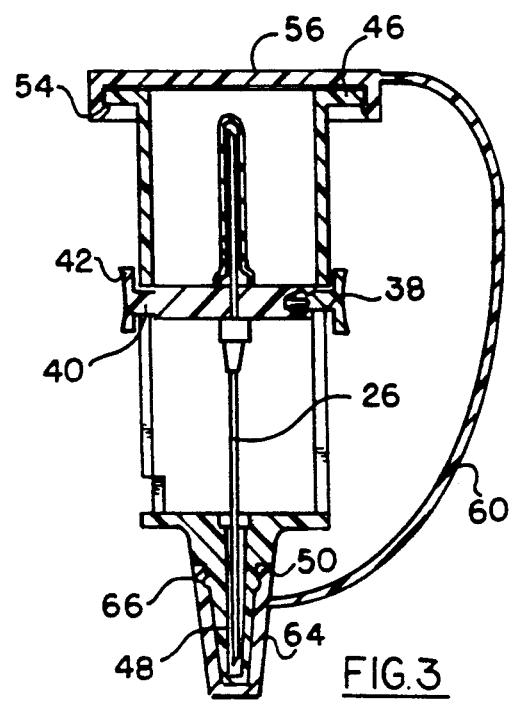
FIG. 3 is a front sectional view of the blood collection device including optional elements such as a tube rear end cap joined by a flexible connector to a needle sheath cap or cover; the front section view presents the device with the double-ended needle in a retracted position for handling, shipping, or discarding. The finger tab is shown as a separate snap-in device installed in the needle support member.

The tube 4 has a needle sheath 48 on the tube forward end 8. FIG. 3 illustrates that the needle sheath 48 can optionally include a holding ring 50 which secures a needle sheath cap or cover 64 to the needle sheath when the double-ended tubular needle 26 is fully retracted. The needle sheath 48, by means of the holding ring 50, secures the sheath cap 64 by interlocking with an interior groove 66 in the sheath cap. In addition, FIG. 3 illustrates an optional tube rear end cap 56 locked in place through the operation of a cap securing lip 54 which when combined with the tube rear handling flange 46 fixes the tube rear end cap to the device for handling and/or disposal. Optionally, the tube rear end cap 56 is joined to the sheath cap 64 by a flexible connector 60.

The tube rear end cap 56 is shown to be larger in size than handling flange 46, allowing the tube rear end cap to cover the handling flange and be secured by means of a snap-fit mechanism. In an alternative embodiment, a snap-fit cap, could involve an inside fitting means, not shown.

In FIG. 4, a perspective view is shown of the apparatus including an exterior tube sleeve 41 having sleeve longitudinal slots 43. The sleeve longitudinal slots 43 are coradial and adjacent to and of equal length to longitudinal slots 18 and 20 in the tube side wall 16. There are no transverse slot extensions present in the exterior sleeve 41. The double-ended needle forward end 28 is shown as fully extended from the needle sheath 48. The finger tabs 42 are depicted in an unlocked position, as the exterior sleeve 41 has not been turned to allow the arms into the slot extensions 22 and into contact with the detention means 45.

In one embodiment of the invention, the novel blood collection device includes the rotatable sleeve positioned inside the needle tube bore. An alternative embodiment involves the use of the rotatable sleeve on the outside of the tube. The sleeve, whether inside or outside the tube, presents no change in the function of the needle support member, slot means or detention means. The construction of the device allows the sleeve to freely rotate co-axially to the needle tube, while at the same time preventing the sleeve from sliding in a direction parallel to the central axis of the needle tube. The purpose of the sleeve, as an optional feature of the invention, is to close the longitudinal external slots through which the finger tabs travel during needle sheathing and unsheathing manipulations. When the finger tabs are twisted into the locked position with the needle either fully extended or fully retracted, the sleeve will cover the slots in the tube wall, thereby minimizing the release of aerosol blood or blood droplets created when an evacuated blood collection tube is removed from the double-ended needle. In addition, the sleeve will minimize the leakage of blood drops which may form if the double-ended needle's self-sealing cover does not close-off the flow of blood when the evacuated blood collection tube is removed.

FIG. 5 presents a side elevation view of the integrated double-ended needle and blood collection device 2, with the hollow needle forward end 28 fully extended from the tube 4. The figure also shows the use of an evacuated phlebotomy blood collection tube 68 having a rubber septum 70 which seals the evacuated tube. When the tube is placed in position on the tubular needle rear end 30, and is forced into contact with and over the tubular needle rear end 30, the resealable needle cover 32 is penetrated as in the septum 70, thereby allowing communication between the tubular needle forward end 28, which is in the patient, and the interior of the evacuated tube. By removing filled tubes and inserting new evacuated tubes 68, multiple samples can be taken without removing the tubular needle forward end 28 from the patient.

When the last blood sample has been taken, the double-ended needle forward end 28 is withdrawn from the patient. To prevent an accidental needle injury and the possible spread of contagious disease from a contaminated needle, the user can unlock the finger tabs 42 and slideably retract the double-ended needle 26 into the tube bore 6. The rear detention means can then be engaged, whereby the double-ended needle is totally enclosed within the device in the retracted position. By grasping the tabs and handling flange as well as the tubular body, the user should never have need for placing fingers in the proximity of the exposed needle.

The double-ended needle can be utilized from readily available commercial sources and removably affixed to the needle support member which will allow the reuse of the remainder of the device with a new double-ended needle. The major benefit of the present invention, however, is the concept of an integrated double-ended needle and blood collection device wherein the needle is resheathed totally within the device for disposal.

It will be appreciated by one skilled-in-the-art that the selection of any given detention means, component size or appearance is generally not critical to the present invention. The sizes and relative angles of the component pieces are selected to optimize the manipulation of the device. The embodiments described herein are intended as examples rather than as limitations. Thus, the description of the invention is not intended to limit the invention to the particular embodiments described in detail, but it is intended to encompass all equivalents and subject matter within the spirit and scope of the invention as described above and as set forth in the following claims.

What is claimed is:

1. A blood collection device, for use with a double-ended needle, comprising:
   a) a tube having forward and rear ends, and at least one longitudinal external slot,
      said longitudinal slot terminating in a first end with a first closed transverse slot extension and terminating in a second end with second closed transverse slot extension,
      said tube rear end terminating with an open tube bore;
   b) a needle sheath, axially aligned with the axis of the double-ended needle, at said tube forward end;
   c) a support member slideably positioned in said tube bore for movement along said tube bore between said forward end of said tube and said rear end of said tube, wherein the double-ended needle may be mounted centrally and perpendicularly through said support member; and
   d) at least one arm means secured to said support member,
      wherein said arm means projects through said longitudinal external slot and is reversibly movable in a slideable manner between said first closed transverse slot extension and said second closed transverse slot extension by means of said longitudinal external slot, and
      wherein said arm means may be moved into said first closed transverse slot extension to rotate and releasably lock said support member in a forward position wherein the needle is exposed for use or into said second closed transverse slot extension to rotate and releasably lock said support member in a rear position wherein the needle is retracted for storage or disposal.

2. The device according to claim 1, wherein said support member is a substantially rigid disc rotatably and slideably encased within said tube bore, wherein said disc has a center axis, axially aligned with the axis of said tube bore, and wherein said disc has two finger tabs connected to said disc by said arm means, said arm means slideably positioned in and through two longitudinal external slots.

3. The device according to claim 1, wherein the double-ended needle rear end is enclosed by a resealable cover.

4. The device according to claim 1, wherein said needle sheath is conical with the conical taper away from said tube forward end.

5. The device according to claim 1, further comprising a needle sheath cap.

6. The device according to claim 5, wherein said needle sheath secures said sheath cap by means of an interlocking holding ring and groove.

7. The device according to claim 1, further comprising a handling flange at said tube rear end.

8. The device according to claim 1, further comprising a tube rear end cap which closes said tube rear end.

9. The device according to claim 8, wherein said tube rear end cap covers a handling flange at said tube rear end.

10. A blood collection device, for use with a double-ended needle, comprising:
a) a tube having forward and rear ends, and at least one longitudinal external slot, said longitudinal slot terminating in a first end with a first closed transverse slot extension and terminating in a second end with second closed transverse slot extension, said tube rear end terminating with an open tube bore;
b) a tube rear end cap which closes said tube rear end, said tube rear end cap joined by a flexible connector to a needle sheath cap;
c) a needle sheath, axially aligned with the axis of the double-ended needle, at said tube forward end;
d) a support member slideably positioned in said tube bore for movement along said tube bore between said forward end of said tube and said rear end of said tube, wherein the double-ended needle may be mounted centrally and perpendicularly through said support member; and
e) at least one arm means secured to said support member,
wherein said arm means projects through said longitudinal external slot and is reversibly movable in a slideable manner between said first closed transverse slot extension and said second closed transverse slot extension by means of said longitudinal external slot, and
wherein said arm means may be moved into said first closed transverse slot extension to rotate and releasably lock said support member in a forward position wherein the needle is exposed for use or into said second closed transverse slot extension to rotate and releasably lock said support member in a rear position wherein the needle is retracted for storage or disposal.

11. A blood collection device, for use with a double-ended needle, comprising:
a) a tube having forward and rear ends, and at least one longitudinal external slot,
said longitudinal slot terminating in a first end with a first closed transverse slot extension and terminating in a second end with second closed transverse slot extension,
said tube rear end terminating with an open tube bore;
b) a needle sheath, axially aligned with the axis of the double-ended needle, at said tube forward end;
c) a support member slideably positioned in said tube bore for movement along said tube bore between said forward end of said tube and said rear end of said tube, wherein the double-ended needle may be mounted centrally and perpendicularly through said support member;
d) a least one arm means secured to said support member,
wherein said arm means projects through said longitudinal external slot and is reversibly movable in a slideable manner between said first closed transverse slot extension and said second closed transverse slot extension by means of said longitudinal external slot, and
wherein said arm means may be moved into said first closed transverse slot extension to rotate and releasably lock said support member in a forward position wherein the needle is exposed for use or into said second closed transverse slot extension to rotate and releasably lock said support member in a rear position wherein the needle is retracted for storage or disposal; and
e) an interior tube sleeve having at least one sleeve longitudinal slot, wherein said sleeve longitudinal slot is opposed to and of equal length to said tube longitudinal external slot, and wherein said interior sleeve is rotatably mounted to close said tube longitudinal external slot.

* * * * *